United States Patent [19]

Lurie et al.

[11] Patent Number: 5,316,907
[45] Date of Patent: May 31, 1994

[54] ENZYMATIC FLUOROMETRIC ASSAY FOR ADENYLATE CYCLASE

[75] Inventors: Keith G. Lurie, Minneapolis, Minn.; Phi Wiegn, Valhalla, N.Y.

[73] Assignee: Regents of the University of Minnesota, Minneapolis, Minn.

[21] Appl. No.: 7,847

[22] Filed: Jan. 22, 1993

[51] Int. Cl.$^5$ .................. C12Q 1/00; G01N 21/76
[52] U.S. Cl. .................................. 435/4; 435/19; 435/21; 435/25; 435/191; 435/195; 435/963; 435/968; 436/63; 436/172; 436/805; 436/811
[58] Field of Search ............ 435/4, 19, 21, 25, 191, 435/195, 963, 968; 436/63, 172, 805, 811

[56] References Cited

PUBLICATIONS

M. M. Bradford et al., "A rapid and sensitive method for the quantitation of microgram quantities of protein utilizing the principle of protein-dye binding", *Anal. Biochem.*, 72, 248 (1976).

McL. Breckenridge, "The measurement of cyclic adenylate in tissues", *PNAS USA*, 52, 1580 (1964).

M. R. Bristow et al., "Decreased catecholomaine sensitivity and B-adrenergic-receptor density in failing human hearts", *New Engl. J. Med.*, 307, 205 (1982).

M. R. Bristow et al., "Histamine-mediated adenylate cyclase stimulation in human myocardium", *Mol. Pharmacol.*, 21, 671 (1982).

N. D. Goldberg et al., "Enzymatic analysis of cyclic 3', 5'-AMP in mammalian tissues and urine", *Anal. Biocheml*, 28 523 (1969).

E. Heimreich et al., "The effects of pH and temperature on the kinetics of the phosphorylase reaction", *Proc. Natl. Acad. Sci. (US)*, 52(3), 647-54 (1964).

E. Heimreich et al., "The role of adenylic acid in the activation of phosphorylase", *Proc. Natl. Acad. Sci. (US)*, 51(1) 131-8 (1964).

C. L. Johnson et al., "Studies on histamine H$_2$ receptors coupled to cardiac adenylate cyclase", *Mol. Pharmacol.*, 16, 417 (1979).

O. H. Lowry et al., *A Flexible System of Enzymatic Analysis*, Academic Press, New York, pp. 129-218 (1972).

O. H. Lowry et al., "Effects of adenylic acid on the kinetics of muscle phosphorylase a", *J. Biol. Chem.*, 239, 1947 (1964).

K. G. Lurie et al., "Increased B-adrenergic receptor density in an experimental model of cardiac transplantation", *J. Thorac. Cardiovasc. Surg.*, 86, 195 (1983).

K. G. Lurie et al., "Metabolism and electrophysiology in subendocardial Purkinje fibers after infraction", *Am. J. Physiol.*, 253, H662-H670 (1987).

F. M. Matschinsky et al., "Quantitative histochemical analysis of glycolytic intermediates and cofactors with an oil well technique", *J. Histochem. Cytochem.*, 16, 29 (1968).

(List continued on next page.)

*Primary Examiner*—Michael G. Wityshyn
*Assistant Examiner*—Abdel A. Mohamed
*Attorney, Agent, or Firm*—Warren D. Woessner

[57] ABSTRACT

A method of measuring adenylate cyclase (AC) in a sample of physiological material which does not employ radioactive reagents is provided, comprising:

(a) providing a physiological sample of physiological material comprising cAMP produced by endogenous AC, and other endogenous adenine nucleotides selected from the group consisting of ATP, AMP, ADP and mixtures thereof;

(b) combining the sample with effective amounts of apyrase, 5'-nucleotidase and adenosine deaminase, so as to enzymatically eliminate the other endogenous adenine nucleotides in the sample;

(c) enzymatically converting the cAMP into AMP; and (d) measuring the amount of AMP, the amount providing a measure of the amount of cAMP and AC in the sample.

15 Claims, 5 Drawing Sheets

PUBLICATIONS

K. J. Rocha-Singh, et al., "Hypoxia and glucose independently regulate the B-adrenergic receptor-adenylate cyclase system in cardiac myocytes", *J. Clinical Investigation*, 88, 204 (1991).

Y. Salomon et al., "A highly sensitive adenylate cyclase assay", *Analy. Biochem.*, 58, 541 (1974).

Y. Salomon et al., "Adenylate Cyclase Assay", *Adv. Cyclic Nucleotide Res.*, 10, 35 (1979).

C. Sungman et al., "Kinetics of cyclic enzyme systems", *Mol. Pharmacol.*, 1, 178 (1965).

M. Trus et al., "Effects of glucose on insulin release and on intermediary metabolism of isolated perifused pancreatic islets form fed and fasted rats", *Diabetes*, 29, 1 (1980).

Rossomando et al., *Proc. Natl. Acad. Sci. USA*, vol. 78, No. 4, pp. 2278-2282, Apr. 1981.

Yoshioka et al., *Journal of Chromatography*, vol. 400, pp. 133-141, 1987.

ENZYMATIC FLUOROMETRIC ASSAY FOR ADENYLATE CYCLASE

BACKGROUND OF THE INVENTION

Adenylate cyclase (ATP pyrophosphate-lyase [cycling], AC, EC 4.6.1.1), the catalytic protein that converts ATP to adenosine 3',5'-cyclic monophosphate (cAMP), plays a critical role in the signal transduction cascade of a number of fundamental hormones and neurotransmitters. For example, measurement of adenylate cyclase activity has been employed to study the altered physiology exhibited by transplanted human hearts and in congestive heart failure. See K. G. Lurie et al., *J. Thorac. Cardiovasc. Surg.*, 86, 195 (1983); M. R. Bristow et al., *New Engl. J. Med.*, 307, 205 (1982) (Chemical names of abbreviated compounds are given in the "Table of Abbreviations", hereinbelow).

However, a more clear elucidation of the biological role of adenylate cyclase in these and other conditions has been limited by the difficulty in monitoring accurately changes in the tissue levels of the cyclic nucleotide. The analytical difficulties arise because of the extremely low concentrations of 3',5'-cAMP in most mammalian tissues and the similarity of this cyclic nucleotide to other naturally occurring, potentially interfering, nucleotides that are present in several hundred to several hundred thousand times the concentration of 3',5'-cAMP.

Adenylate cyclase activity is conventionally assayed indirectly by measuring the synthesis of radioactively labeled cAMP from the substrate $\alpha$-$^{32}$P-labeled ATP as described by Y. Salomon et al., as disclosed in *Anal. Biochem.*, 58, 541 (1974) and *Adv. Cyclic Nucleotide Res.*, 10, 35 (1979). The methods employ sequential affinity chromatography with Dowex exchange resin and aluminum oxide columns to separate newly generated [$^{32}$P]cAMP from [$\alpha$-$^{32}$P]ATP. See also, C. L. Johnson et al., *Mol. Pharmacol.*, 16, 417 (1979). Although this method is sensitive, it relies upon costly radioactively labeled compounds.

Previously, Lowry et al. have developed a number of sensitive assays which can measure small amounts of biological compounds based on the fluorescence of reduced pyridine nucleotides. See O. H. Lowry et al., *A Flexible System of Enzymatic Analysis*, Harcourt Brace Jovanovich, NY (1972); F. M. Matschinsky et al., *J. Histochem. Cytochem.*, 16, 29 (1968). These methods employ one or more of a series of enzymatic reactions which ultimately lead to the production of either $\beta$-nicotinamide-adenine dinucleotide phosphate (NADP$^+$) or $\beta$-nicotinamide-adenine dinucleotide (AND$^+$) or the reduced forms NADPH and NADH. The reduced purine nucleotides can be precisely measured at O.D. 340 nm in the photometer. One reaction, the measurement of AMP, depends upon the stimulatory effects of AMP on glycogen phosphorylase a, the enzyme that converts glycogen into glucose-6-phosphate in the presence of inorganic phosphate ($P_i$). See, E. Helmreich et al., *Biochemistry*, 52, 647 (1964); ibid., 51, 131 (1964); O. H. Lowry et al., *J. Biol. Chem.*, 239, 1947 (1964); M. Trus et al., *Diabetes*, 29, 1 (1980). Attempts to increase the analytical sensitivity and specificity for AMP or AC have involved the enzymic degradation of interfering nucleotides and/or their removal by chromatography (See N. D. Goldberg et al., *Anal. Biochem.*, 28, 523 (1969); B. McL. Breckenridge, *PNAS USA*, 52, 1580 (1964)). However, fluorometric assays have not been developed which can either directly or indirectly measure adenylate cyclase activity in physiological samples needed to accurately quantify AC or cAMP in $\mu$g samples at pmol or fmol levels.

Given the safety and environmental concerns associated with the use and disposal of radioactive materials used in the current methods to measure AC, a need exists for a highly sensitive nonradioactive assay to measure adenylate cyclase activity.

SUMMARY OF THE INVENTION

The present invention provides a highly sensitive, enzymatic fluorometric or spectrophotometric assay for adenylate cyclase (AC) activity present in a sample of physiological material, such as a tissue or fluid sample, which necessarily contains other adenins nucleotides, in addition to the cAMP produced from ATP by the AC present in the sample. The present assay method first comprises the enzymatic destruction of the adenins nucleotides other than cAMP (ATP, ADP and AMP) with a mixture of apyrase, 5'-nucleotidase and adenosine deaminase. The cAMP is then converted to AMP with phosphodiesterase. The resulting AMP, in turn, can be quantified by a number of methodologies, such as those which employ it in the enzymatic conversion of an added substrate to NADPH. Thus, the present assay is based on the combination of the complete dephosphorylation of the non-cyclic nucleotides, followed by subsequent deamination, so that the dephosphorylation reactions are driven to completion.

To quantify AMP, the AMP can be used to stimulate the activity of added glycogen phosphorylase a which converts added glycogen and inorganic phosphate into glucose-1-phosphate. The glucose-1-phosphate is ultimately enzymatically converted into 6-phosphogluconolactone, NADPH and H$^+$. The NADPH concentration is then determined fluorometrically, i.e., in accord with the methodology of M. Trus et al., *Diabetes*, 29, 1 (1980).

Optionally, the 6-phosphogluconolactone can itself be further converted to 6-phosphogluconate by heating it in the presence of an aqueous medium, i.e., in situ and the 6-phosphogluconate can be converted to NADPH, H$^+$, CO$_2$ and ribulose-5-phosphate, in situ, in the presence of added NADP$^+$. The reactions and reagents employed in this embodiment of the present method are summarized on Table 1, below.

TABLE 1

| AC Assay |
|---|
| 1. Cleaning Reaction |
| a. ATP $\xrightarrow{\text{Apyrase}}$ AMP + 2 $P_i$ |
| b. AMP + H$_2$O $\xrightarrow{\text{5'Nucleotidase}}$ adenosine + $P_i$ |
| c. Adenosine + H$_2$O $\xrightarrow{\text{adenosine deaminase}}$ inosine + NH$_4^+$ |

TABLE 1-continued
AC Assay

2. cAMP Reactions cAMP + H$_2$O $\xrightarrow{\text{phosphodiesterase}}$ AMP
$\downarrow$ a. glycogen + P$_i$ $\xrightarrow{\text{glycogen phosphorylase a}}$
   glucose-1-phosphate b. glucose-1-phosphate $\xrightarrow{\text{phosphoglucomutase}}$
   glucose-6-phosphate c. glucose-6-phosphate +
   NADP $\xrightarrow{\text{glucose-6-phosphate dehydrogenase}}$
   6-phosphogluconolactone + NADPH + H$^+$

3. Optional Reactions d. 6-Phosphogluconolactone + H$_2$O $\xrightarrow{\text{Heat}}$
   6-Phosphogluconate + H$^+$ e. 6-Phosphogluconate +
   NADP$^+$ $\xrightarrow[\text{Dehydrogenase, Mg}^{2+}]{\text{6-Phosphogluconate}}$ Ribulose-5-P +
   NADPH + H$^+$ + CO$_2$ The production of ammonium ion in deamination reaction 1(c) drives the cleaning reaction sequence essentially to completion, preventing reformation of interfering phosphorylated nucleotides.

The physiological material which is assayed in accord with the present method is preferably obtained from a mammalian source, including tissue, blood cells, bone and physiological fluids such as urine, blood, CSF and the like. Preferably, the cAMP in the sample is provided in situ, by the conversion of endogenous and/or exogenously added ATP to cAMP by endogenous adenylate cyclase (AC). Samples as small as 10 µg can be used in the present method.

Thus, in a preferred embodiment, the present invention comprises the steps of:
(a) providing a sample of a physiological material comprising cAMP and at least one other (noncyclic) adenine nucleotide, i.e., selected from the group consisting of ATP, ADP, AMP and mixtures thereof;
(b) forming a reaction mixture by combining said sample with an aqueous buffer comprising a mixture of 5'-nucleotidase, apyrase, and adenosine deaminase, so that said adenine nucleotide (the ATP, ADP and/or AMP) is destroyed, while the cAMP is retained in the resulting reaction mixture;
(c) combining said reaction mixture with phosphodiesterase, so that said cAMP is converted to AMP.
(d) contacting said AMP with glycogen phosphorylase in the presence of glycogen and inorganic phosphate so that glucose-1-phosphate is produced in said reaction mixture;
(e) enzymatically converting the glucose-1-phosphate into 6-phosphonogluconolactone, NADPH and H$^+$ in said reaction mixture; and
(f) fluorometrically measuring the concentration of NADPH in said reaction mixture; and correlating said concentration of NADPH with the concentration of AC, cAMP or AMP in said sample.

The correlation of the end-concentration of NADPH to the AMP concentration or the cAMP concentration is simplified by our finding that the stimulation of glycogen phosphorylase a by cAMP and AMP is similar in magnitude. In situations in which the cAMP in the sample is produced from endogenous or exogenous ATP by endogenous AC, said AC activity at any time point in the conversion reaction can also be measured (e.g., in pmol/mg of tissue), for example, following stimulation of AC activity by endogenous agonists.

Preferably, following step (b), the enzymes used in the cleaning reaction deactivated, i.e., by heating or by the addition of acid or base.

Preferably, an aqueous "cAMP mixture" of phosphodiesterase, glycogen phosphorylase a, glucose-1,6-diphosphate, inorganic phosphate, glycogen, NADP$^+$ Mg$^{2+}$, glucose-6-phosphate dehydrogenase and, phosphoglucomutase is added to the reaction mixture, following the "cleaning reaction" of step (b), which carries out steps (c), (d) and (e), sequentially, in situ.

Optionally, the concentration of NADPH which is generated in step (e) can be increased by sequentially converting the 6-phosphogluconolactone to 6-phosphogluconate by heating the aqueous reaction mixture of step (e), and then reacting the 6-phosphogluconate with added NADP$^+$ and 6-phosphogluconate dehydrogenase in the presence of Mg$^{2+}$ to yield ribulose-5-phosphate, NADPH, H$^+$ and CO$_2$, as shown in Table 1, hereinabove.

Alternatively, the effective concentration of NADPH which is generated in step (e) can be increased in orders of magnitude by employing it in a cycling reaction system. One such reaction system converts NADPH added to α-ketoglutarate into NADP$^+$ and glutamate, which in turn converts added glucose-6-phosphate into 6-phosphogluconolactone + NADPH. As described above, the 6-phosphogluconolt lactone can be hydrolyzed (H$_2$O, heat) and converted to ribulose-5-P and NADPH, using 6-phosphogluconate dehydroIgenase and Mg$^{2+}$. The reactions employed in this cycling system, which is described in detail in O. Lowry et al., A Flexible System of Enzymatic Analysis, Academic Press, NY (1972), as depicted below on Table 1A:

TABLE 1A

α-Ketoglutarate + NADPH + NH$_4^+$ $\xrightarrow[\text{Dehydrogenase}]{\text{Glutamate}}$
Glutamate + NADP$^+$ Glucose-6-P + NADP$^+$ $\xrightarrow[\text{Dehydrogenase, Mg}^{2+}]{\text{Glucose-6-P}}$
6-Phosphonogluconolactone + NADPH + H$^+$ Alternatively, as shown in Table 1B, the AMP which is produced in step (c) can be converted to ADP by combining it with ATP in the presence of myokinase. The ADP which is produced is then converted to ATP and pyruvate by combining the ADP with 2-phospho(enol)pyruvate (PEP) and pyruvate kinase (PK). The ATP is then employed in cycling reaction depicted in Table 1B.

TABLE 1B

I ATP Reaction

AMP + ATP $\xrightarrow{\text{Myokinase}}$ 2 ADP

TABLE 1B-continued $$2\ ADP + 2\ Phospho(Enol)Pyruuvate \xrightarrow{Pyruvate\ Kinase} 2\ ATP + 2\ Pyruvate$$

II. ATP Cycling Reaction

Hexokinase cycle: Fructose → Fructose-6-Phosphate, with ATP/ADP cycling between Pyruvate and Phospho(Enol)Pyruvate $$Fructose\text{-}6\text{-}Phosphate \xrightarrow{Phosphoglucose\ isomerase} Glucose\text{-}6\text{-}Phosphate$$

$$Glucose\text{-}6\text{-}Phosphate + NADP^+ \xrightarrow{Glucose\text{-}6\text{-}Phosphate\ Dehydrogenase} 6\text{-}Phosphogluconolactone + NADPH + H^+$$

The resulting fructose-6-phosphate, produced from the excess fructose and PEP used in the cycling reaction, is converted to glucose-6-phosphate using phosphoglucose isomerase, and the glucose-6-phosphate is converted into 6-phosphogluconolactone and NADPH by exposing the G-6-P to glucose-6-phosphate dehydrogenase and $NADP^+$. The NADPH concentration can then be amplified using the cycling reaction of Table 1A.

Another method to measure AMP comprises the conversion of AMP into ATP and the use of ATP to convert excess added glucose into glucose-6-phosphate, which is in turn converted into 6-phosphogluconolactone and NADPH with glucose-6-phosphate dehydrogenase. See B. McL. Breckenridge, *PNAS USA*, 52, 1580 (1964). Alternatively, ATP could subsequently be amplified by converting excess glucose and excess $NADP^+$ to glucose-6-P and NADPH, as described in O. Lowry et al., *A Flexible System of Enzymatic Analysis*, cited above. NADPH is then increased by orders of magnitude by the cycling system described in Table 1A.

The present assay method can readily be adapted to measure guanylate cyclase activity, guanosine 3',5'-cyclic monophosphate (cGMP) and guanosine 3', 5'-monophosphate (GMP). As shown on Table 1C, below, a cleaning mixture of apyrase, 5'-nucleotidase, nucleoside phosphorylase and guanase is used. In the cleaning reactions, tissue GTP is converted to GMP plus 2Pi, GMP plus water is converted into guanosine and Pi, guanosine plus Pi is converted into guanine and ribose-1-phosphate and guanine plus water is converted into xanthine and ammonia. As in the cleaning reaction depicted in Table 1, the formation of ammonium (or $NH_4^+$) in the final cleaning reaction drives the series of linked reactions essentially to completion, and ensures removal of the interfering nucleotides. Preferably, the enzymes used in the cleaning reactions are deactivated, e.g., by heating, prior to the phosphodiesterase step (2).

TABLE 1C cGMP Reactions

1. Cleaning Reactions

TABLE 1C-continued cGMP Reactions $$GTP \xrightarrow{Apyrase} GMP + Pi$$

$$GMP + H_2O \xrightarrow{5'Nucleotidase} Guanosine + Pi$$

$$Guanosine + Pi \xrightarrow{Nucleoside\ Phosphorylase} Guanine + Ribose\text{-}1\text{-}P$$

2) Phosphodiesterase Step:

$$cGMP \xrightarrow{Phosphodiesterase} GMP$$

$$GMP + ATP \xrightarrow{Guanine\ Monophosphate\ Kinase} GDP + ADP$$

3) Cycling Reactions:

Pyruvate Kinase / Succinic Thiokinase cycle: Phospho(Enol)Pyruvate → Pyruvate with GDP/GTP cycling; Succinate + CoA → Succinate-CoA + Pi 4) Indicator Reaction:

$$Pyruvate + NADH + H^+ \xrightarrow{Lactate\ Dehydrogenase} Lactate + NAD^+$$

The cGMP present in the (tissue) sample is then converted to GMP with phosphodiesterase. The GMP is combined with ATP in the presence of guanine monophosphate kinase to yield guanosine 5'-diphosphate (GDP) and ADP. The GDP is employed in a cycling reaction (3) in the presence of excess PEP, succinate-CoA and inorganic phosphate (Pi) to yield an amount of pyruvate. This pyruvate is quantitated indirectly by adding known amounts of NADH which, in the presence of acid, is converted to lactate and $NAD^+$. Thus, the fluorescence of the indicator samples is decreased in direct proportion to the amount of pyruvate generated in the sample to be assayed for cGMP, GMP or guanylate cyclase.

In addition to improving assay sensitivity, measurement of adenylate cyclase activity or guanylate cyclase activity with the present enzymatic assays is significantly less costly, less time consuming, safer for the operator, and better for the environment. Thus, they offer a significant methodological advance for the measurement of adenylate cyclase or guanylate cyclase activity.

Finally, the present assay can readily be adapted to determine the amount of endogenous or exogenous phosphodiesterase in a sample, such as a physiological sample. In accord with this embodiment of the invention, a single, preselected amount of cAMP is added to a sample containing an unknown concentration of phosphodiesterase. Specific inhibitors of specific phosphodiesterases can be added as needed. A standard curve is generated by adding a single, preselected excess amount of cAMP to different preselected, known amounts of phosphodiesterase. After a finite amount of reaction time (5-60 minutes) in which some but not all of the added cAMP is transformed to AMP by the phosphodiesterase, the reaction is stopped. A cAMP standard curve can be run concurrently to verify that all reactions are working adequately. A cleaning reaction is initiated to degrade all old and newly generated non-cyclic adenine nucleotides, as described above. The remaining cAMP will be inversely proportional to the native plus added phosphodiesterase. The cAMP is then measured in the usual manner, i.e., converted to AMP and assayed.

The present invention also provides as an article of manufacture, a kit comprising packaging material, such as a box, containing in association, separately packaged, preselected amounts of (a) apyrase, 5'-nucleotidase and adenosine deaminase or (b) apyrase, 5'-nucleotidase, nucleoside phosphorylase and guanase; and wherein said kit includes instruction means which indicate that (1) said separately packaged amounts of the three enzymes listed in part (a) can be used to remove the non-cyclic phosphorylated nucleotides shown in Table 1(1) above, from cAMP, in an assay for cAMP, AC activity, AMP or mixtures thereof, in accord with the present invention; or (2) said separately packaged enzymes listed in part (b) can be used to remove the non-cyclic phosphorylated nucleotides shown in Table 1C(1) from cGMP, in the assay for cGMP, guanylate cyclase activity or GMP in accord with the present invention.

Suitable instruction means include printed labels, printed package inserts, tags, cassette tapes, and the like. Suitable packaging material for the enzymes includes bottles, vials and the like. Optionally, the enzymes may be pre-mixed with an acceptable liquid vehicle, such as a physiological buffer.

DETAILED DESCRIPTION OF THE INVENTION

Figure 1:
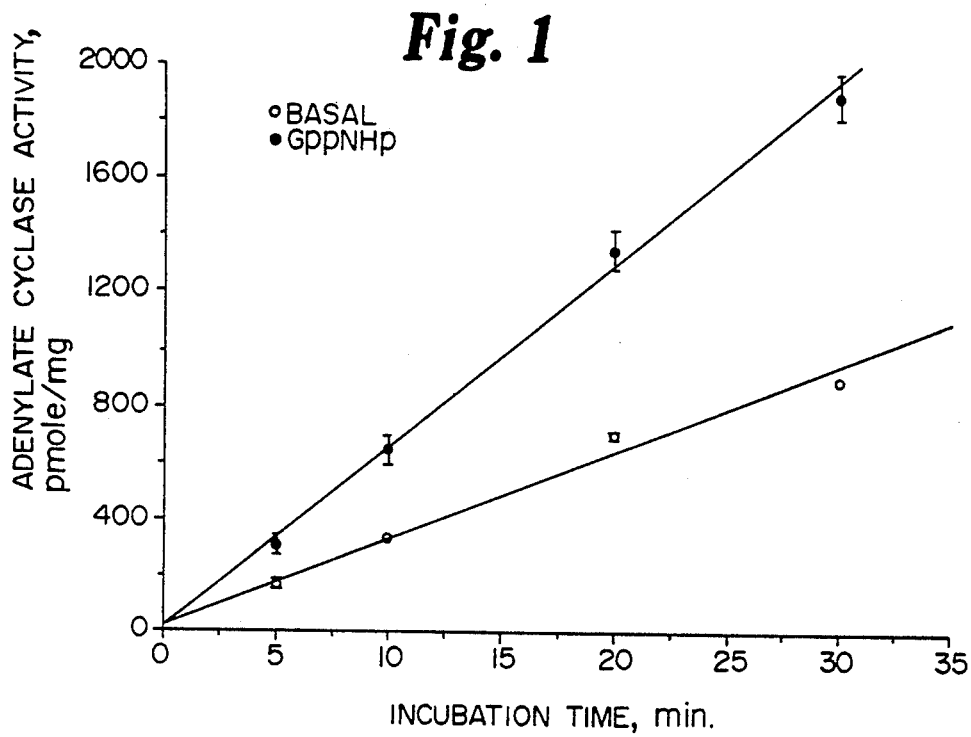
FIG. 1 is a graphical depiction of the time course of basal (○) and GppNHp (●)-stimulated tissue AC activity as measured by a prior art assay.

The present invention provides a novel, nonradioactive enzymatic fluorometric assay for adenylate cyclase activity which offers several advantages over currently available methods. Unlike the assays previously disclosed by Y. Salomon et al., in *Anal. Biochem.*, 58, 541 (1974) and *Adv. Cyclic Nucleotide Res.*, 10, 35 (1979), the present assay does not utilize any radioactive material. In addition, this assay is more sensitive and simpler to perform than the previous assays.

Lowry and others have previously developed and employed a highly sensitivity method to measure AMP, as disclosed by, for example, K. Lurie et al., *Am. J. Physiol.*, 253, H662-H670 (1987). AMP-stimulated glycogen phosphorylase a activity is dependent upon temperature and the concentrations of glycogen, inorganic phosphate, and glycogen phosphorylase a. See, E. Heimreich et al., *Biochemistry*, 51, 131 (1964) and M. Trus et al., *Diabetes*, 29, 1 (1980). One embodiment of the present fluorometric measurement of cAMP is based on the principle that AMP, generated from the cleavage of the 3', 5'-phosphodiester linkage of cAMP, will stimulate glycogen phosphorylase a activity. There was, in fact, essentially no difference between glycogen phosphorylase a activation when its stimulation with AMP was compared to its stimulation with cAMP in the presence of phosphodiesterase.

The cleaning step in the present fluorometric cAMP assay removes all endogenous ATP, ADP, and AMP which would otherwise substantially increase the blank. It is essential for satisfactory assay sensitivity. As demonstrated in the working examples, the sensitivity of this assay can also be increased by reducing the reaction volumes. It can also be increased further by varying the concentrations of glycogen and inorganic phosphate in the reaction mix, as taught by Heimreich et al. and E. Helmreich et al., *Biochemistry*, 52, 647 (1964). With the present level of sensitivity, measurement of agonist-stimulated adenylate cyclase activity is possible in mammalian tissue biopsy samples comprising as little as 10.0 μg of membrane protein. Unlike the radioactive methods, where sensitivity is limited by the specific activity of [α-$^{32}$P]cAMP and the volume size for chromatographic separation, there are no significant barriers to further increasing the sensitivity of the present fluorometric method. For example, cAMP has been measured with fluorometric enzyme-linked reactions which are sensitive over a broad concentration range of cAMP (50 fmol-1 mmol).

When stimulated adenylate cyclase activity was measured in the same preparations from rabbit heart with both the modified Salomon radioactivity method and the present fluorometric method, the results were similar (Examples 1-2). Results with the radioactive assay are comparable to results K. Lurie et al. have previously reported using rabbit heart preparations (*J. Thorac. Cardiovasc. Surg.*, 86, 195 (1983)). Although the absolute specific activities are different when the results from the radioactive and fluorometric assays are compared, the fold stimulation of AC as determined using either method is similar. The differences in specific activities are most likely due to minor variations in the adenylate cyclase reaction mixes. Specifically, unlabeled cAMP is used in the radioactive assay to prevent [$^{32}$P]cAMP degradation by endogenous phosphodiesterases, whereas theophylline is used in the fluorometric assay to inhibit endogenous phosphodiesterase degradation of newly synthesized cAMP.

The invention will be further described by reference to the following detailed examples wherein the enzymes, substrates, and cofactors used were obtained from Boehringer Mannhelm Co. except for apyrase and 5'-nucleotidase which were obtained from Sigma Co., St. Louis, Mo.). The [$\alpha$-$^{32}$P]ATP, $^{3}$H-cAMP, and Aquasol scintillation cocktail were purchased from New England Nuclear. Neutral Chromatographic Alumina WN-3 was obtained from Bio-Rad.

Ventricular membrane preparations were prepared from five male New Zealand white rabbits (weight 2.4 kg; W.O.R.K., Philomith, Oreg.) sacrificed by cervical concussion and immediate incision of the heart as previously described (10). Briefly, hearts were placed in ice-cold SET buffer (0.25M sucrose, 0.1 mM EDTA, 5.0 mM Tris-HCl, pH 7.4). Portions (1-2 g) from the ventricular apex were minced and then homogenized in ice-cold SET buffer (1/10, w/v). The homogenate was filtered through a Nitex filter (three layers) (Tetko, Los Angeles, Calif.) and then centrifuged for 20 min at 1000×g. The pellet was resuspended and centrifuged three more times. The final pellet was resuspended in SET buffer (1.5 mg protein/ml) and stored at −70° C. until enzyme activity was measured.

EXAMPLE 1

RADIOACTIVE ADENYLATE CYCLASE ASSAY

A volume of 1.0 μl of either H$_2$O, NaF, guanylyl-5'-imidodiphosphate (GppNHp), isoproterenol, or isoproterenol+GppNHp was added to each reaction tube and maintained at 0° C. Next, 25 μl of reaction mixture A (Tris Acetate 100 mM, pH 7.4; KCl mM; MgCl$_2$ 10.0 mM; phosphoenolpyruvate 20 mM; ATP 2.0 mM; GTP 0.02 mM; dithiothreitol 2.0 mM; bovine serum albumin 0.04%; cAMP 0.66 mM, pyruvate kinase 1.0mg/ml, and $\alpha$-$^{32}$P-ATP, 3000 Ci/mmole) were added to each reaction tube. Finally, 25 μl of membrane suspension (40 to 45 μg protein) were added to each tube and the reaction was initiated by placing the tubes in a water bath at 37° C. After 30 minutes, the reaction was terminated by the addition 300 μl of a stopping solution which contained 0.34N HCl and $^{3}$H-cAMP, 10,000-20000 cpm.

Figure 2:
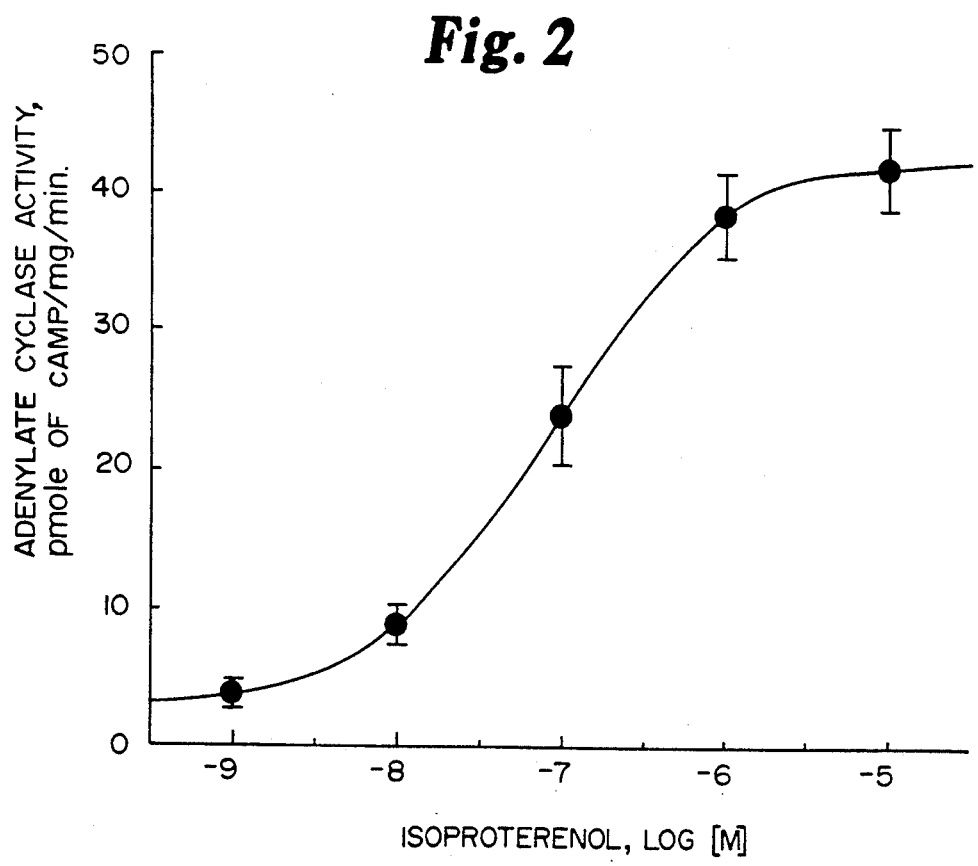
FIG. 2 is a graphical depiction of the level of tissue AC activity following stimulation of tissue AC activity by isoproterenol, as measured by a prior art assay.

To generate the graph depicted in FIG. 2, 250 μl portions of reaction mixture A and membrane were used and 50 μl samples were removed from the 37° C. bath every 10 minutes, and stopped with 300 μl stopping solution. The assay tubes were heated at 95° C. for 5 minutes. $^{32}$P-cAMP was isolated using Dowex-alumina chromatography. Recovery, as assessed by $^{3}$H-cAMP, was 80-95%. All assays were conducted in triplicate. The time course of adenylate cyclase activity (n=5 different rabbit ventricular membrane preparations) is depicted in FIG. 1. Basal AC and agonist-stimulated (0.1 mM GppNHp, 0.1 mM) AC are compared. Measurements of isoproterenol-stimulated AC activity (in the presence of GppNHp, a GTP analog) are shown in FIG. 2. The activity shown is (isoproterenol+GppNHp-stimulated AC activity) minus (GppNHp-stimulated activity).

EXAMPLE 2

FLUOROMETRIC ADENYLATE CYCLASE ASSAY

Part A

The first part of the non-radioactive fluorescent technique for measuring adenylate cyclase activity is similar to the method described above except that theophylline, rather than unlabeled cAMP, was used to inhibit phosphodiesterase activity. A volume of 1.0 μl of either H$_2$O, NaF, guanylyl-5'-imidodiphosphate (GppNHp), isoproterenol, or isoproterenol+GppNHp was added to each reaction tube and maintained at 0° C. Next, 25 μl of reaction mixture B (Tris Acetate 100 mM, pH 7.4; KCl 20 mM; MgCl$_2$ 10.0 mM; phosphoenolpyruvate 20 mM; ATP 2.0 mM; GTP 0.02 mM; dithiothreitol 2.0 mM; bovine serum albumin 0.04%; theophylline 0.2 mM; pyruvate kinase 1.0mg/ml) were added to each reaction tube. Finally, 25 μl of membrane suspension (40 to 45 μg protein) were added to each tube and the reaction was initiated by placing the tubes in a water bath at 37° C. After 30 minutes at 37° C, the reaction was stopped by the addition of 50 μl of 50 mM NaOH. The reaction mixture was heated for 5 minutes at 95° C. For cAMP standards, a known amount of cAMP was added to either 25 μl of boiled membrane preparation or 25 μl H$_2$O and then this mixture was added to 25 μl of reaction mixture B. After 30 minutes, the reaction was stopped by the addition of 50 μl of 50 mM NaOH, and the reaction mixture was heated for 5 minutes at 95° C.

Part B

Newly synthesized cAMP was measured as follows:
1. A volume of 20-40 μl of reaction product from Part A was added to 100 μl of cleaning reaction mix (Tris-HCl 50 mM, pH 8.0, MgCl$_2$ 5 mM, CaCl$_2$ 2.0 mM, 5'-nucleotidase, 2.5 units/ml; apyrase, 2 units/ml; adenosine deaminase 0.1 mg/ml). After 30 minutes at 37° C., the reaction was terminated by heating it at 95° C. for 5 minutes.

2. A volume of 300 μl of cAMP mix (Imidazole-HCl 50 mM, pH 6.9; MgCl$_2$, 0.5 mM; EGTA, 1.0 mM; BSA, 0.004%; inorganic phosphate, 1.5 mM; glycogen (0.1 mM of glucose reduction units), glucose-1,6-diphosphate, 2 uM; NADP+, 0.15 mM; dithiothreitol (DTT), 0.5 mM; phosphodiesterase [beef heart] 0.1 mg/cc, glucose-6-phosphate dehydrogenase, 15 μg.ml; phosphoglucomutase, 30 μg/ml; glycogen phosphorylase a, 6.7 μg/ml). After 60 minutes at 37° C., 600 μl of 2-amino-2-methyl-1-propanol (AMP$_2$), 50 mMM, pH 9.9 was added to the reaction mix and the final concentration of NADPH was measured fluorometrically.

Protein analysis was performed by the methods of Bradford et al. using bovine serum albumin as standard (M. M. Bradford et al., *Anal. Biochem.*, 72, 248 (1976)). All data was expressed as mean±S.E.M.

Figure 3:
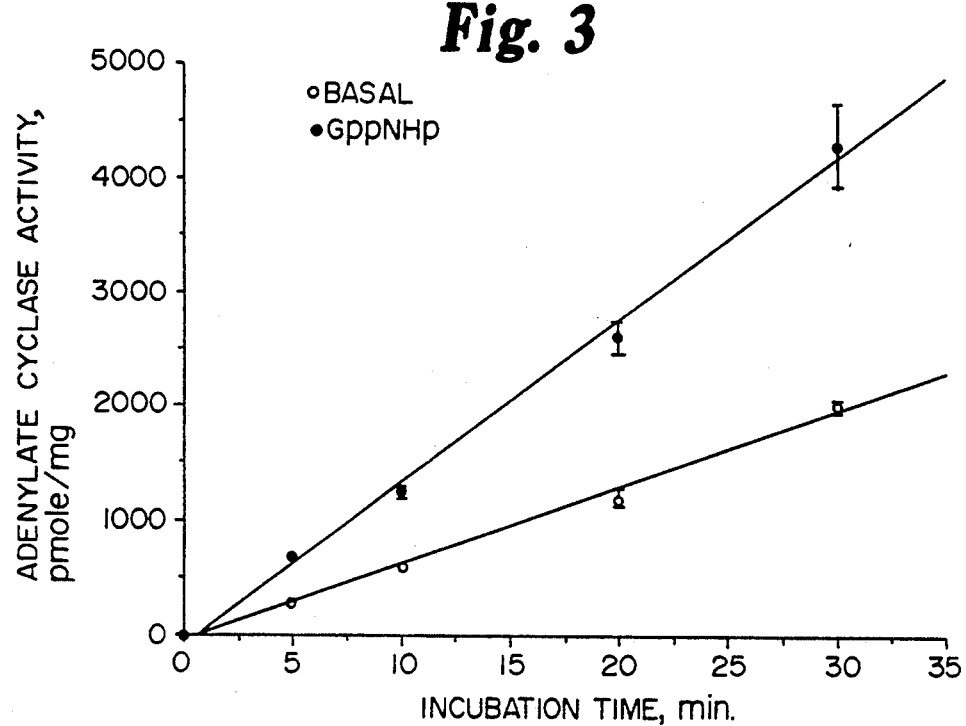
FIG. 3 is a graphical depiction of the time course of basal (○) and GppNHp (●)-stimulated tissue AC activity as measured by an embodiment of the assay of the invention.

FIG. 3 depicts the time course of AC activity (n=5 different rabbit ventricular membrane preparations) obtained using this method. To generate these data, 250 μl of reaction mixture B was added to 250 μl of plasma membrane. The reaction proceeded at 37° C. and samples (25 μl) were removed every 10 minutes. A volume of 25 μl of 0.05N NaOH was added and heated at 90° C.

for 5 minutes and cAMP was measured. Basal adenylate cyclase and agonist-stimulated activity (GppNHp, 0.1 mE) are compared.

Figure 4:
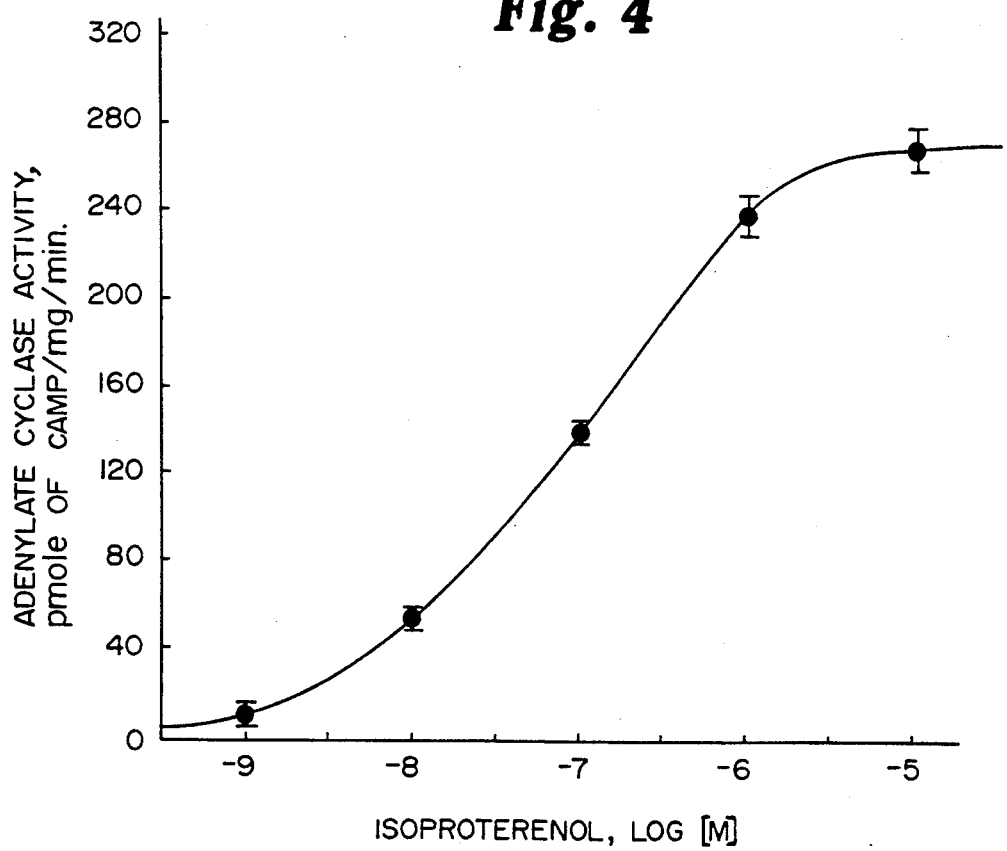
FIG. 4 is a graphical depiction of the level of tissue AC activity following stimulation of tissue AC activity by isoproterenol, as measured by an embodiment of the assay of the invention.

FIG. 4 depicts the adenylate cyclase activities in response to different doses of isoproterenol in the presence of 0.1 mM of GppNHp (n=5 different rabbit heart preparations). The activity shown here is (isoproterenol+GppNHp-stimulated adenylate cyclase activity) minus (GppNHp-stimulated activity).

The time course for adenylate cyclase activity using both radioactive and fluorometric methods yielded similar results (FIGS. 1 and 3). The absolute amount of cAMP generated/mg/minute is different with these reactions. However, when activation by GppNHp($10^{-4}$M) is expressed as a percent of basal activity, the time courses of basal- and agonist-stimulated cAMP production are nearly identical.

Measurements of isoproterenol-stimulated adenylate cyclase activity (in the presence of GppNHp, a GTP analog) using the radioactive and fluorometric methods is shown in FIGS. 2 and 4. Although the absolute values for adenylate cyclase activity are different, when these results are expressed as a percent increase over basal activity ("fold stimulation"), the curves are nearly identical.

EXAMPLE 3

EFFECT OF THEOPHYLLINE ON BASAL ADENYLATE CYCLASE ACTIVITY

To investigate the effects of theophylline on basal adenylate cyclase activity, increasing concentrations of theophylline were studied (Table 2).

TABLE 2

| [Theophylline] | Basal (no isoproterenol) (pmole/mg/min.) | Fold Increase[a] | Isoproterenol Stimulated[b] (pmole/mg/min.) | Fold Increase |
|---|---|---|---|---|
| Control | 30.67 ± 8.30 | — | 51.73 ± 10.47 | — |
| 10 μM | 44.72 ± 4.61 | 1.46 | 85.58 ± 5.56 | 1.65 |
| 50 μM | 44.63 ± 5.93 | 1.46 | 93.02 ± 3.55 | 1.80 |
| 100 μM | 59.94 ± 3.63 | 1.91 | 104.21 ± 3.50 | 2.01 |
| 500 μM | 53.82 ± 4.37 | 1.75 | 102.67 ± 2.86 | 1.98 |

[a]Fold Increase = Basal activity/activity in the presence of Theophylline
[b]Isoproterenol-stimulated = Isoproterenol at $10^{-6}$M
n = 5

With theophylline at 100–500 μM, basal activity is increased approximately 100%. However, the "fold" stimulation (agonist-stimulated activity/basal activity of adenylate cyclase activity was constant at a given concentration of agonist (isoproterenol) in the presence of theophylline. When theophylline was added at concentrations greater than 100 μM, no significant increase in basal activity was observed.

EXAMPLE 4

COMPARASION OF AC ASSAYS

Table 3 demonstrates the similarities in measurement of adenylate cyclase activity after agonist stimulation when the radioactive and fluorometric assays were used in 5 preparations of rabbit ventricle. Although the basal activity is nearly 3 times higher in the nonradioactive method, the "fold" stimulation is similar for both receptor-mediated agonists (isoproterenol±GppNHp) as well by NaF, which directly stimulates adenylate cyclase.

TABLE 3

| Agonist | Radioactive Adenylate Cyclase Assays (n = 5) (pmoles of cAMP/mg/min) | Fold Increase[a] | Fluorescent Adenylate Cyclase Assays (n = 5) (pmoles of cAMP/mg/min) | Fold Increase |
|---|---|---|---|---|
| Basal | 20.7 ± 1.4 | — | 65.4 ± 6.8 | — |
| Iso[b] | 38.3 ± 2.3 | 1.85 | 110.0 ± 3.3 | 1.68 |
| GppNHp[c] | 64.9 ± 3.3 | 3.13 | 185.3 ± 13.7 | 2.83 |
| Iso + GppNHp[d] | 96.9 ± 5.3 | 4.68 | 263.7 ± 9.3 | 4.03 |
| NaF[e] | 106.2 ± 3.5 | 5.13 | 346.7 ± 15.9 | 5.30 |

[a]Fold Increase = Agonist stimulated activity/Basal activity
[b]Iso = Isoproterenol at $10^{-6}$M
[c]GppNHp = 5'-Guanylyl-imidodiphosphate at $10^{-4}$M
[d]Iso + GppNHp = Isoproterenol at $10^{-6}$M plus 5'-Guanylyl-imidodiphosphate at $10^{-4}$M
[e]NaF = Sodium Fluoride at $10^{-2}$M The non-radioactive assay is at least 5 times more sensitive than the modified Salomon radioactive assay of Example 1. In Table 3, 5 μl of membrane preparation were used to measure adenylate cyclase activity in the nonradioactivity assay compared to 25 μl with the radioactive preparations. In a separate experiment, the volume of membrane suspension was reduced from 25 μl to 5 μl. By proportionally reducing the assay volume size, no difference in basal (58.4±3.9), isoproterenol ($10^{-6}$M) (128±7.6) or NaF ($10^{-2}$M) (331.9±42.8) stimulated activity was observed when results were compared to larger assay volumes present.

EXAMPLE 5

STIMULATION OF GLYCOGEN PHOSPHORYLASE BY cAMP AND AMP

A glycogen→NADPH model reaction system was prepared by combining 100 mM imadazole·HCl, pH 6.9; 0.5 mM MgCl₂, 1.0 mM EGTA; 0.5 mM DTT; 2 μM glucose-1,6-diphosphage, 0.02% BSA, 1 mM Pi, 0.3 mM glycogen, 0.3 mM NADP+, 0.5 μg/ml phosphodiesterase [beef heart], 10 μg/ml glucose-6-phosphate dehydrogenase, 20 μg/ml phosphoglucomutase and 1 μg/ml glycogen phosphorylase a. Ten minutes after initiation of the glycogen-phosphorylase a reaction at 25° C., either cAMP (5 μM) or AMP (5 μM) was added to 1.0 ml of the reaction mixture. Fluorometric readings were taken every 5.0 min. as described in Part B of Example 2, hereinabove.

Figure 5:
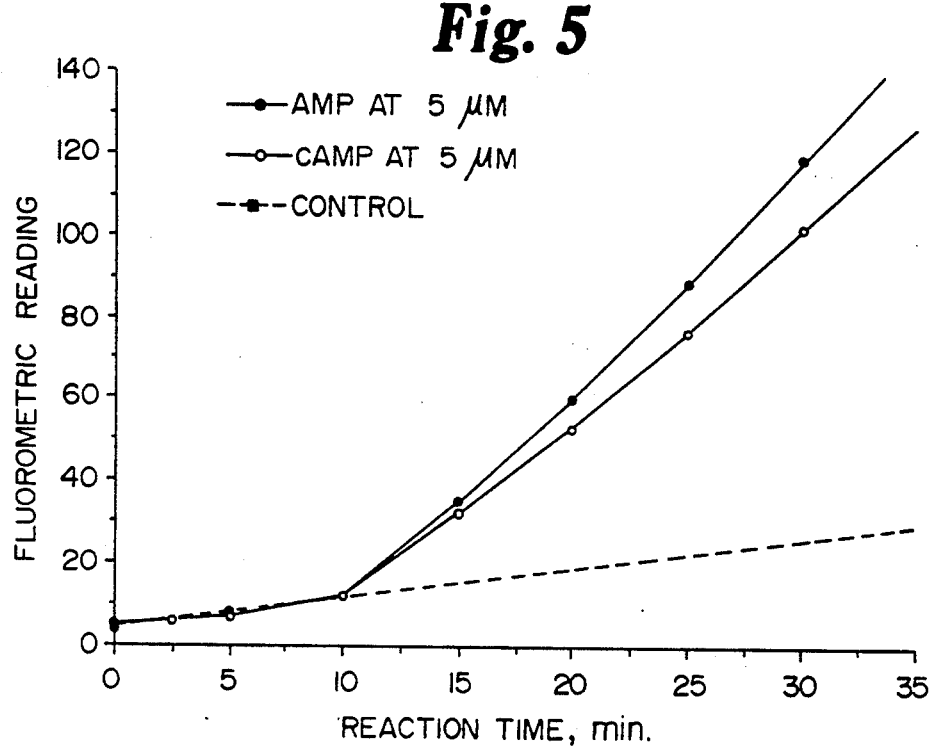
FIG. 5 is a graphical depiction of the time course of NADPH fluorescence produced by stimulation of glycogen phosphorylase a by AMP (○), cAMP (●) and control buffer (■).

As shown in FIG. 5, without AMP or cAMP, the basal reaction in control buffer remained low. The present fluorometric assay for AC activity relies on the principle that stimulation of glycogen phosphorylase a by AMP results in a concentration-dependent increase in phosphorylase a activity by reducing the $K_m$ for both glycogen and phosphate. As can be seen from the data presented in FIG. 5, the activation of glycogen phosphorylase a by cAMP is essentially identical to that caused by AMP.

EXAMPLE 6

REMOVAL OF AMP BY THE CLEANING REACTIONS

Figure 6:
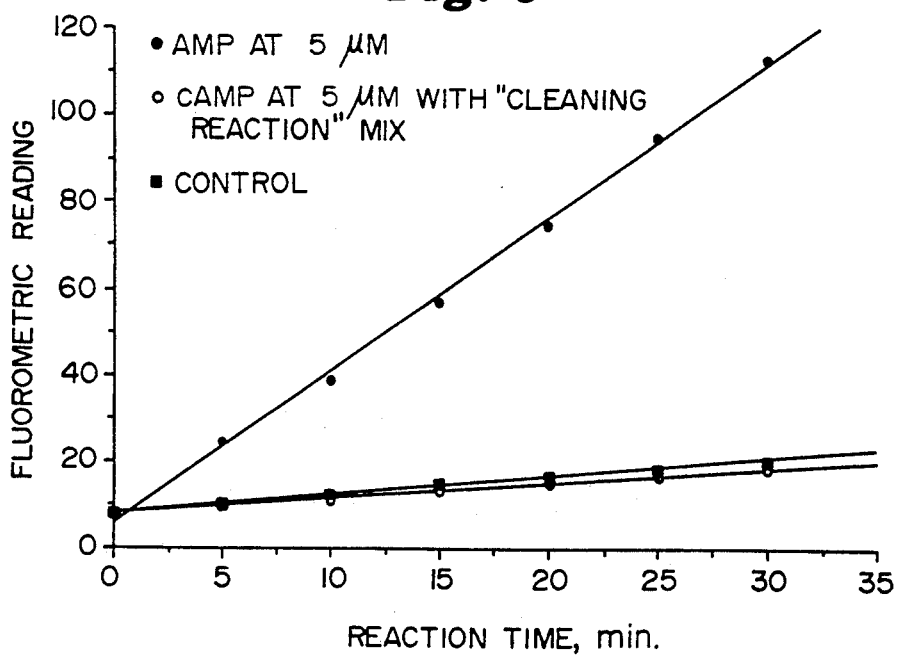
FIG. 6 is a graphical depiction of the time course of NaDPH fluorescence produced by stimulation of glycogen phosphorylase a by AMP (●), AMP with prior pretreatment with "cleaning reaction" mixture (○), and control buffer (■).

The effectiveness of the enzymatic "cleaning reactions" shown in Table 1 is demonstrated by the kinetic data shown in FIG. 6. AMP was incubated for 60 min at 37° C. with 50 μl of either buffer (100 mM Tris-HCl, pH 8.0) or a cleaning reaction mixture containing 100 mM Tris-HCl, pH 8.0; 5 mM MgCl$_2$, 2 mM CaCl$_2$, 2 units/ml apyrase; 2.5 units/ml 5'-nucleotidase and 0.1 mg/ml adenosine deaminase. After heating at 90° C. for 5 min, 950 μl of the glycogen→NADPH "cAMP mixture" of Example 2 was added, and the reaction allowed to proceed at 25° C.

The data on FIG. 6 demonstrate that when AMP is added to this reaction system without the cleaning step, glycogen phosphorylase a activity is markedly stimulated. However, when AMP is added in the presence of the cleaning reaction mixture, glycogen phosphorylase a activity remains similar to the control buffer values, due to the degradation of the AMP.

EXAMPLE 7

FLUOROMETRIC cAMP MEASUREMENT IN TISSUE

The following example illustrates the methodology employed to measure endogenous cAMP fluorometrically in tissue without agonist stimulation of cAMP synthesis.

Frozen heart tissue (0-1000 mg) was homogenized in ten volumes of 2°-4° C. 0.1M NaOH and 2.0 μl portions of the homogenate distributed into five reaction tubes. To each tube was added 4, 8 and 16 pmoles cAMP, as an internal control. To create the standard curve for cAMP, 0, 4, 8 and 16 pmoles of cAMP were added to five tubes each containing 2.0 μl 0.2M NaOH.

Into these tubes was introduced 25 μl of the cleaning reaction mixture shown on Table 4.

TABLE 4

| Compound | Cleaning Reaction Mixture Concentration | Use (3.0 ml) |
| --- | --- | --- |
| Tris-HCl pH 8 | 50 mM | 150 μl |
| MgCl$_2$ | 5 mM | 75 μl |
| CaCl$_2$ | 2 mM | 30 μl |
| 5'Nucleotidase | 2.5 μ/ml | 30 μl |
| Apyrase | 2 μ/ml | 30 μl |
| Adenosine Deaminase | .1 mg/ml | 30 μl |
| H$_2$O |  | 2.70 ml |

All tubes were incubated for 30 min at 37° C., and then heated at 95° C. for 15 minutes. Then, 200 μl of the cAMP reaction mixture shown on Table 5 was added to each tube.

TABLE 5

| Compound | cAMP Reaction Mixture Concentration | Use (25.0 ml) |
| --- | --- | --- |
| Imidazole pH 6.9 | 50 mM | 1.25 ml |
| MgCl$_2$ | 0.5 mM | 63 μl |
| EGTA | 1 mM | 250 μl |
| BSA | 0.004% | 25 μl |
| K$_2$HPO$_4$ | 1.5 mM | 38 μl |
| Glycogen | 0.25 mM | 438 μl |
| G-1,6-P | 2 μM | 50 μl |
| NADP$^+$ | 0.15 mM | 38 μl |
| DTT | 0.5 mM | 125 μl |
| Phosphodiesterase | 13.5 μg/ml | 33.8 μl |
| G-6-Pi-Dehydrogenase | 2.5 μg/ml | 11.3 μl |

TABLE 5-continued

| Compound | cAMP Reaction Mixture Concentration | Use (25.0 ml) |
| --- | --- | --- |
| Phosphogluco-Mutase | 4.5 μg/ml | 11.3 μl |
| Glycogen Phosphorylase a | 2.2 μg/ml | 8.0 μl |
| H$_2$O |  | 22.7 ml |

Figure 7:
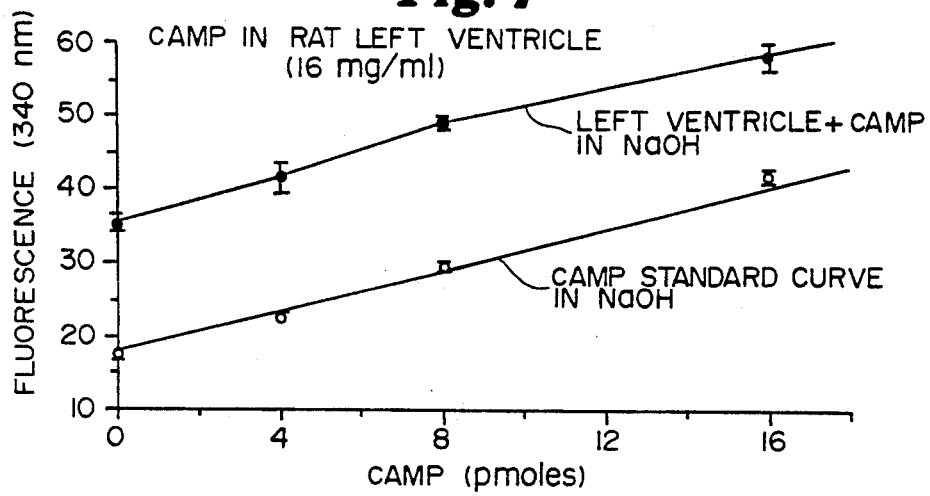
FIG. 7 is a graphical depiction of the fluorescence measured for left ventricle tissue samples plus added cAMP in NaOH (●) and of the fluorescence measured for standard cAMP samples in NaOH(○), in accord with the present method.

The tubes were incubated for 90 minutes at 31° C., 800 μl of AMP$_2$ buffer (50 mM, pH 9.9) was added, and the fluorescence measured at 340 nm. The data was plotted to yield the graph of FIG. 7, which yielded a plot (●) for the internal controls that was consistently elevated above the cAMP standard plot. From this plot, it could be determined that this tissue sample contained 12 pmol of cAMP.

EXAMPLE 8

MICRO-cAMP MEASUREMENT IN TISSUE

This example illustrates an adaptation of the present assay so that cAMP can be measured in the range of 0-1000 fmol. The assay comprises amplifying the NADPH formed by the reactions shown on Table 1, hereinabove, using a cycling system utilizing glucose-6-P dehydrogenase and glutamate dehydrogenase, as generally disclosed by O. Lowry et al., in *Flexible System of Enzymatic Analysis*, Academic Press, NY (1972) at pages 130-135.

Frozen rat heart tissue is sectioned (20 μ thick) in a cryostat and freeze-dried at −40° C. Pieces of tissue from four different regions of the heart (six pieces/region), (2-4 μg each) are cut and placed in Teflon® block wells. To each piece, 0.2 μl of 20 mM aqueous NaOH is added. To generate standard curves, cAMP samples in the appropriate range (0, 40, 80, 160 and 320 and 0, 125, 250, 500 and 1000 fmol/0.2 μl) are prepared in 20 mM NaOH and pipetted into eight other wells. All of the wells are then covered with a mixture of 40% n-hexadecane and 60% light mineral oil to prevent evaporation. The wells are heated to 80° C. for 20 minutes and then cooled to 25° C. Cleaning reaction mixture (Table 6) (0.4 μl) is added to each well and the reaction allowed to proceed for 30 min. at 37° C., then stopped by heating at 80° C. for 30 minutes.

TABLE 6

| Compound | Cleaning Reaction Mixture Concentration | Use |
| --- | --- | --- |
| Tris HCl pH 8.0 | 75 mM | 30 μl |
| MgCl$_2$ | 5 mM | 10 μl |
| CaCl$_2$ | 2 mM | 4 μl |
| 5'Nucleotidase | 5 μ/ml | 8 μl |
| Apyrase | 2 μ/ml | 8 μl |
| Adenosine Deaminase | 4 μ/ml | 8 μl |
| Glucose-oxidase | 50 μ/ml | 4 μl |
| α-Amylase | 63 μ/ml | 10 μl |
| H$_2$O |  | 338 μl |

To all wells, 0.6 μl of cAMP reaction mixture (Table 7) is added and the wells incubated for 2 hours at 31° C.

TABLE 7

| Compound | cAMP Reaction Mixture Concentration | Use |
| --- | --- | --- |
| Imidazole pH 6.9 | 75 mM | 375 μl |
| MgCl$_2$ | 0.5 mM | 12.5 μl |
| EGTA | 2 mM | 100 μl |
| Glycogen | 0.2 mM | 14.7 μl |
| BSA | 0.01% | 12.5 μl |

TABLE 7-continued

| cAMP Reaction Mixture | | |
|---|---|---|
| Compound | Concentration | Use |
| DTT | 0.5 mM | 25 µl |
| G-1, 6-P | 2 µM | 10 µl |
| NADP+ | 0.3 mM | 15 µl |
| Pi | 0.2 mM | 10 µl |
| H₂O | | 4.41 ml |
| Phosphodiesterase | 300 µg/ml | 12 µl |
| Glucose-6-Pi-Dehydrogenase | 25 µg/ml | 2 µl |
| Phosphogluco-Mutase | 50 µg/ml | 2 µl |
| Glycogen Phosphorylase a | 2 µg/ml | 8 µl |

At the completion of the incubation, one µl of 0.45N NaOH is added to each well and the wells are again heated for 30 minutes at 80° C.

One µl reaction mixture from each well is transferred into 10×75 mm fluorometric tubes. The internal cycling reaction standards (0, 1, 2 and 4) pmoles NADP+, are prepared in duplicate, as shown in Table 8, and assayed in separate tubes concurrently as a control.

TABLE 8

| Cycling Reaction Standards | | |
|---|---|---|
| | NADP+ (0.5 µM) | |
| Tube | Vol. | Concentration |
| 1-2 | 0 µl | 0 pmoles |
| 3-4 | 2 µl | 1 pmoles |
| 5-6 | 4 µl | 2 pmoles |
| 7-8 | 8 µl | 4 pmoles |

Fifty µl of the cycling reaction mixture (Table 9) are added to each tube, and the tubes are incubated at 37° C. for 60 min.

TABLE 9

| Cycling Reaction Mixture (5 ml) | | |
|---|---|---|
| Compound | Working | Use |
| Tris-Acetate pH 8.0 | 0.1 M | 500 µl |
| Ammonium acetate | 10 mM | 50 µl |
| α-Ketoglutarate | 10 mM | 500 µl |
| BSA | 0.04% | 50 µl |
| G-6-P | 10 mM | 500 µl |
| ADP | 1 mM | 50 µl |
| Glutamate-Dehydrogenase | 30 µg/ml | 15 µl |
| Glucose-6-Pi-Dehydrogenase | 5 mg/ml | 5 µl |
| H₂O | | 3.35 ml |

The rack containing the tubes is placed in a 95° C. water bath for 5 minutes. Indicator reaction standards, 0-4 nmoles 6-PG, are prepared in duplicate, as shown on Table 10, and are assayed in separate tubes concurrently as a control.

TABLE 10

| Indicator Reaction Standards (6-P-G, 0.5 mM) | | |
|---|---|---|
| Tube | Vol. | Concentration |
| 1-2 | 0 µl | 0 nmoles |
| 3-4 | 2 µl | 1 nmoles |
| 5-6 | 4 µl | 2 nmoles |
| 7-8 | 8 µl | 4 nmol |

Each tubes then receives 900 µl of indicator reaction mixture (Table 11) and are allowed to incubate for 30 min at 25° C. The fluorescence is then measured at 340 nm.

TABLE 11

| Indicator Reaction Mixture (100 ml) | | |
|---|---|---|
| Compound | Conc. | Use |
| Tris-HCl pH 8.0 | 50 mM | 5 ml |
| EDTA | 0.1 mM | 50 µl |
| Ammonium acetate | 30 mM | 3 ml |
| MgCl₂ | 5 mM | 2.5 ml |
| NADP+ | 0.2 mM | 200 µl |
| 6-Pi-Gluconate-Dehydrogenase | 2.5 µg/ml | 25 µl |
| H₂O | | 91.925 ml |

Figure 8:
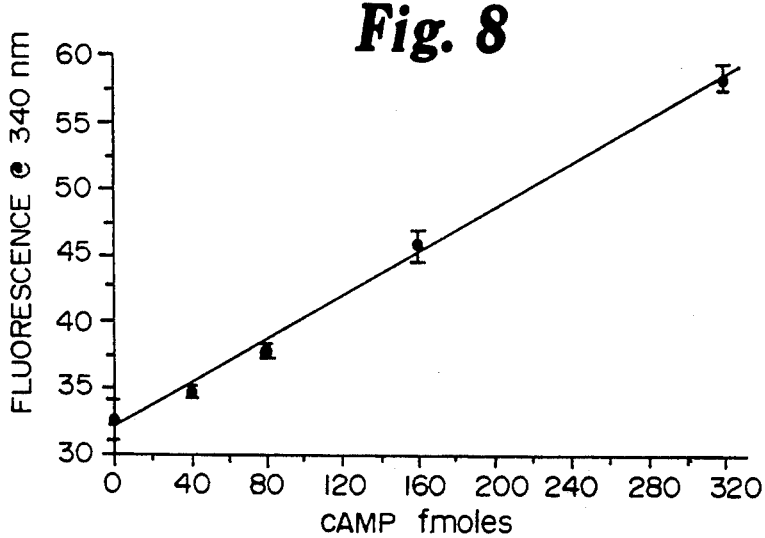
FIG. 8 is a graphical plot of fluorescence against concentration of standard samples of cAMP as determined by an embodiment of the invention.
Figure 9:
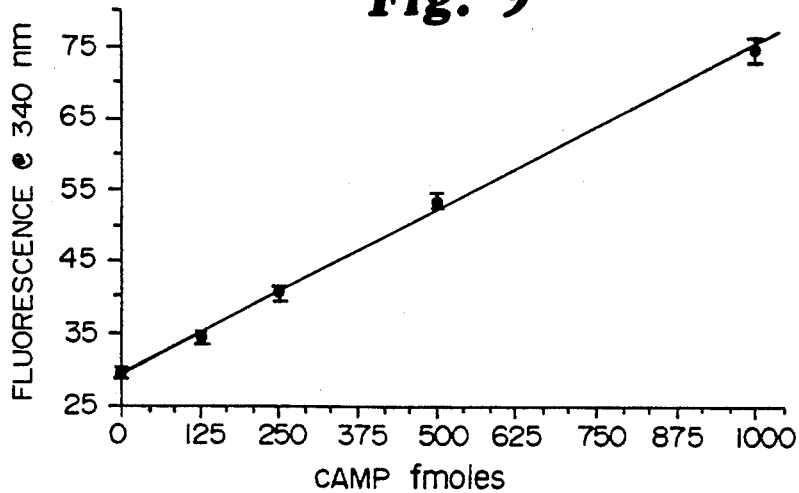
FIG. 9 is a graphical plot of fluorescence against concentration of standard samples of cAMP as determined by an embodiment of the invention.
Figure 10:
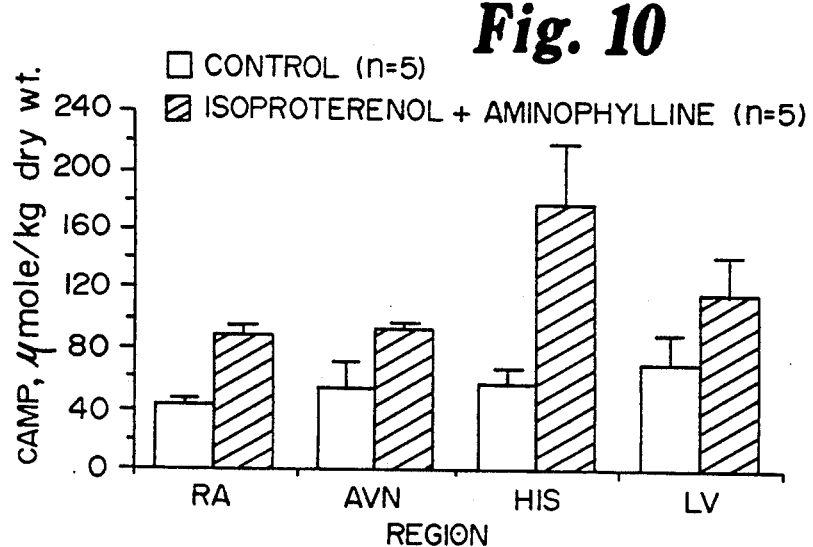
FIG. 10 is a graphical plot of the amount of cAMP in four regions of the rat heart (untreated=clear; drug-treated=shaded) as determined by the present method.

As depicted in FIGS. 8 and 9, the fluorescence measured for the control cAMP samples yielded linear plots over 40–1000 fmoles of cAMP. As shown in FIG. 10, when performed on tissue from five rats (control) or five rats pretreated 15 min before sacrifice with 0.33 µg/kg isoproterenol plus 20 µg/kg aminophylline, this assay is effective to measure the cAMP concentration in four regions of the heart (right atrium—RA; atrioventricular node—AVN; his bundle—HS; and the left ventricule—LV).

EXAMPLE 9

MICRO cAMP MEASUREMENT IN TISSUE WITH ATP-ADP DOUBLE CYCLING

Frozen tissue is sectioned (20 microns thick) in a cryostat and freeze-dried at −40° C. Six pieces, weighing 2-4 µg, for each tissue type are cut and placed into Teflon block wells, and aqueous of 20 mM NaOH (0.2 µl) is added to each well. cAMP standards (0, 125, 250 and 507 fmoles/0.2 µl) are prepared in 20 mM NaOH and pipetted into three wells (one well contains only 0.2 µl NaOH). All of the Teflon wells are then covered with oil (40% n-Hexadecane and 60% Light Mineral Oil). The aqueous mixtures are heated at 80° C. for 30 minutes and then allowed to cool to 25° C. To all wells, 0.4 µl of cleaning reaction mixture of Table 12 is added and the reaction allowed to proceed for 60 minutes at 37° C., then heated at 80° C. for 30 minutes.

TABLE 12

| Cleaning Reaction Mixture | | |
|---|---|---|
| Compound | Final Reaction Concentrations | Use |
| Tris HCl pH 8.0 | 75 mM | 30 µl |
| MgCl₂ | 5 mM | 10 µl |
| CaCl₂ | 2 mM | 4 µl |
| 5'Nucleotidase | 5 µ/ml | 8 µl |
| Apyrase | 2 µ/ml | 8 µl |
| Adenosine Deaminase | 4 µ/ml | 8 µl |
| H₂O | | 332 µl |
| | | 400 µl |

To all wells, 0.6 µl of the pyruvate kinase reaction mixture of Table 13 is added and the Teflon block is incubated for 120 minutes at room temperature.

TABLE 13

| PK Reaction Mixture | | |
|---|---|---|
| Compound | Final Reaction Concentrations | Use |
| Imidazole pH 6.9 | 100 mM | 500 µl |
| MgCl₂ | 2 mM | 50 µl |
| KCl | 50 mM | 250 µl |
| Phospho(Enol)Pyruvate | 5 mM | 50 µl |
| Bovine Serum Albumin | 0.01% | 12.5 µl |
| Dithiothreitol | 0.5 mM | 25 µl |
| ATP | 150 nM | 75 µl |
| H₂O | | 4.0 ml |
| Pyruvate Kinase | 20 µg/ml | 2 µl |

TABLE 13-continued

PK Reaction Mixture

| Compound | Final Reaction Concentrations | Use |
|---|---|---|
| Myokinase | 4 µg/ml | 2 µl |
| Phosphodiesterase | 20 µg/ml | 2 µl |

At the completion of this incubation, 1 µl of First Cycling Mix of Table 14 is added to each well and the reaction mixtures incubated for 60 minutes at 25° C.

TABLE 14

First Cycling Mixture

| Compound | Final Reaction Concentrations | Use |
|---|---|---|
| Tris-HCl pH 8 | 50 mM | 50 µl |
| KCl | 50 mM | 50 µl |
| MgCl$_2$ | 2 mM | 100 µl |
| Fructose | 5 mM | 50 µl |
| Bovine Serum Albumin | .01% | 2.5 µl |
| NADP+ | .2 mM | 2 µl |
| Hexokinase | 47 µg/ml | 4.7 µl |
| Phosphoglucoe Isomerase | 40 µg/ml | 4 µl |
| Glucose-6-Phosphate dehydrogenase | 10 µg/ml | 2 µl |
| H$_2$O | | 734.8 µl |
| | | 1.0 ml |

To all wells, 1 µl of 0.45N NaOH is added and the Teflon block is heated at 80° C. for 30 minutes. Two µl from each well is transferred into fluorometric tubes. Cycling reaction standards, 0–4 pmoles NADP+, were prepared in duplicate, as shown on Table 14, to serve as a control.

TABLE 15

Cycling Rx Standards +(NADP 0.5 µM)

| Tube No. | Vol. | Conc. |
|---|---|---|
| 1-2 | 0 µl | 0 pmoles |
| 3-4 | 2 µl | 1 pmoles |
| 5-6 | 4 µl | 2 pmoles |
| 7-8 | 8 µl | 4 pmoles |

To all tubes, 50 µl of the Second Cycling Reaction Mix of Table 16 is added, and the tubes incubated at 37° C. for 60 minutes, then the rack containing the tubes is placed in a 95° C. water bath for 5 min.

TABLE 16

Second Cycling Mix

| Compound | Final Reaction Concentrations | Use |
|---|---|---|
| Tris-Acetate pH 8.0 | 0.1 M | 500 µl |
| Ammonium acetate | 10 mM | 50 µl |
| α-Ketoglutarate | 10 mM | 500 µl |
| Bovine Serum Albumin | 0.04% | 50 µl |
| Glucose-6-Phosphate | 10 mM | 500 µl |
| ADP | 1 mM | 50 µl |
| Glutamate dehydrogenase | 30 µg/ml | 15 µl |
| Glucose-6-Phosphate dehydrogenase | 5 µg/ml | 5 µl |
| H$_2$O | | 3.35 ml |
| | | 5.0 ml |

Indicator reaction standards, 0–4 nmoles 6-phosphogluconolactone (6-PG), are prepared in duplicate, as shown on Table 17, as a control.

TABLE 17

Indicator Rx Standards (6-P-G 0.5 mM)

| Tube | Vol. | Conc. |
|---|---|---|
| 1-2 | 0 µl | 0 nmoles |
| 3-4 | 2 µl | 1 nmoles |
| 5-6 | 4 µl | 2 nmoles |
| 7-8 | 8 µl | 4 nmol |

All tubes receive 900 µl of indicator mix of Table 18, and are allowed to incubate for 30 minutes at 25° C.

TABLE 18

Indicator Reaction Mix

| Compound | Final Reaction Concentrations | Use |
|---|---|---|
| Tris-HCl pH 8.0 | 50 mM | 5 ml |
| EDTA | 0.1 mM | 50 µl |
| Ammonium acetate | 30 mM | 3 ml |
| MgCl$_2$ | 5 mM | 2.5 ml |
| NADP+ | 0.2 mM | 200 µl |
| 6-Phospho Gluconate dehydrogenase | 2.5 µg/ml | 25 µl |
| H$_2$O | | 91.925 ml |
| | | 100.0 ml |

Figure 11:
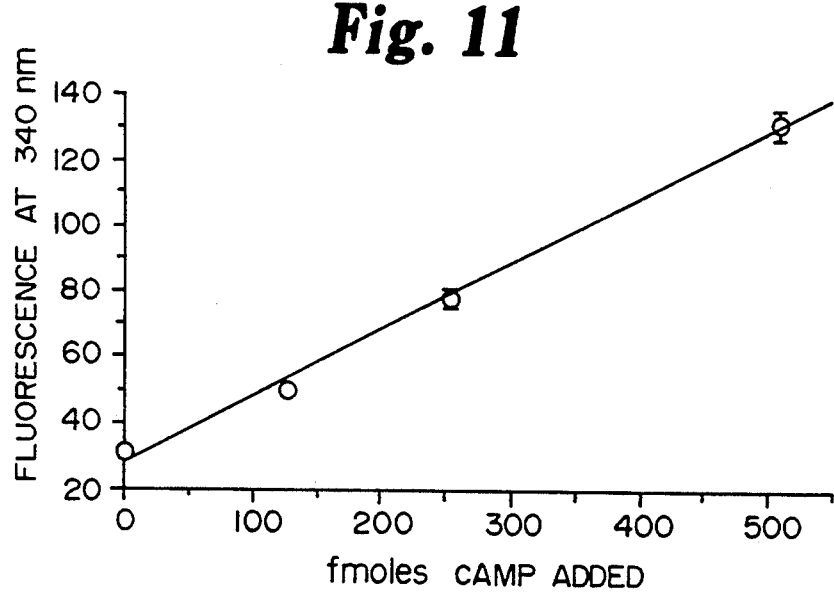
FIG. 11 is a graphical plot of fluorescence against concentration of standard samples of cAMP as determined by an embodiment of the invention.

The fluorescence is measured at 340 nm, to afford the standard curve shown on FIG. 11, demonstrating the ability of the present assay to quantify cAMP in the fmol range.

TABLE OF ABBREVIATIONS

| Abbreviation | Chemical Name |
|---|---|
| ATP | adenosine 5'-triphosphate |
| ADP | adenosine 5'-diphosphate |
| AMP | adenosine 2'- and 3'-monophosphate |
| AC | adenylate cyclase |
| GTP | guanosine 5'-triphosphate |
| cAMP | adenosine 3',5'-cyclic monophosphate |
| Gpp(NH)p | guanylyl-5'-imidodiphosphate |
| EGTA | ethyleneglycol-bis-(β-aminoethyl ether)-N,N'-tetraacetic acid |
| AMP$_2$ | 2-amino-2-methylpropanol |
| BSA | bovine serum albumin |
| DTT | dithiothretol |
| ME | β-mercaptoethanol |
| Tris | tris(hydroxymethyl)aminoethane |
| NADP | β-nicotinamide adenine dinucleotide phosphate |
| NADPH | β-nicotamide adenine dinucleotide phosphate (reduced form) |
| PEP | phospho(enol)pyruvate |
| PK | phosphokinase |
| G-6-P | glucose-6-phosphate (or glucose-6-P) |
| P$_i$ | inorganic phosphate |
| GGPDH | glucose 6-phosphate dehydrogenase |
| GDH | glutamic dehydrogenase |
| G-1,6-P | glucose-1,6-diphosphate |
| G-6-P$_i$-dehydrogenase | glucose-6-phosphate-dehydrogenase |

All publications and patents are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A method measuring adenylate cyclase (AC) activity in a sample of physiological material comprising:
   (a) combining a sample of physiological material comprising cAMP produced by endogenous AC and other endogenous adenine nucleotides selected from the group consisting of ATP, AMP, ADP and mixtures thereof with effective amounts of apyrase, 5'-nucleotidase and adenosine deaminase, to enzymatically eliminate said other endogenous adenine nucleotides in said sample;

(b) enzymatically converting the cAMP into AMP; and (c) measuring the amount of AMP without the use of radioactive reagents, said amount providing a measure of the amount of cAMP and AC in said sample.

2. The method of claim 1, wherein, in step (b), said AMP is employed to stimulate the enzymatic production of an amount of NADPH which is proportional to the amount of AMP present in the sample; and wherein in step (c) fluorometry, spectrofluorometry or spectrophotometry is employed in measure said amount of NADPH, to provide a measure of the adenylate cyclase and cAMP in said sample.

3. The method of claims 1 or 2 wherein excess glucose-6-phosphate, excess α-ketoglutonate, glutamate dehydrogenase and glucose-6-phosphate dehydrogenase are combined with the amount of NADPH prior to fluorimetry so that the α-ketoglutarate is converted to glutamate and NADP+, and the glucose-6-P and the NADP+ are converted to 6-phosphogluconolactone and NADPH.

4. The method of claim 3 wherein said 6-phosphonogluconolactone is further hydrolyzed to 6-phosphogluconate and said 6-phosphogluconate is combined with NADP+ in the presence of 6-phosphogluconate dehydrogenase to yield ribulose-5-phosphate and NADPH 5. The method of claims 1 or 2 wherein the physiological material is mammalian tissue.

6. The method of claims 1 or 2 wherein the physiological material is a physiological fluid.

7. The method of claim 1 wherein the conversion of cAMP into AMP is carried out by combining the sample with an effective amount of phosphodiesterase.

8. The method of claim 1 wherein step (b) further comprises the conversion of glycogen and inorganic phosphate added to the sample to glucose-1-phosphate by added glycogen phosphorylase a, which is stimulated by said AMP in situ.

9. The method of claim 8, wherein in step (b), the glucose-1-phosphate is converted into 6-phosphogluconolactone and NADPH by combining the sample with an amount of phosphoglucomutase effective to convert the glucose-1-phosphate to glucose-6-phosphate, and by combining the sample with an amount of glucose-6-phosphate dehydrogenase and NADP+ effective to convert the glucose-6-phosphate to 6-phosphogluconolactone and NADPH.

10. The method of claim 9 further comprising, in step (b), heating the sample in the presence of water, so as to convert the 6-phosphogluconolactone into 6-phosphogluconate, and adding an amount of NADP+ to said sample which is effective to convert the 6-phosphogluconate into ribulose-6-phosphate and NADPH.

11. A fluorometric method to measure adenylate cyclase (AC) comprising:

(a) combining a sample of a physiological material comprising cAMP produced by endogenous AC, and at least one other noncyclic adenine nucleotide with a mixture of apyrase, 5'-nucleotidase and adenosine deaminase in aqueous buffer to destroy at least one other adenine nucleotide, while retaining said cAMP in the resulting reaction mixture;

(b) converting said cAMP to AMP by combining said reaction mixture with phosphodiesterase, glycogen, glycogen phosphorylase a, inorganic phosphate, phosphoglucomutase, glucose-6-phosphate dehydrogenase, glucose-1,6-diphosphate, $Mg^{2+}$ and NADP+ so that said glycogen is converted into NADPH and 6-phosphonogluconolactone; and (c) measuring the concentration of NADP fluorometrically, said concentration of NADPH providing a measure of the concentration of cAMP and AC in said sample.

12. The method of claims 1 or 11 wherein the enzymes of step (b) are deactivated following destruction of the noncyclic nucleotides.

13. The method of claim 11 wherein steps (a) and (b) are combined.

14. The method of claims 11 or 8 further comprising, after step (b), converting said 6-phosphogluconolactone to ribulose-5-phosphate and NADPH by sequentially heating the reaction mixture and adding 6-phosphogluconate dehydrogenase and NADP+ to the reaction mixture.

15. The method of claim 11 wherein said at least one other adenine nucleotide in step (a) is selected from the group consisting of ATP, ADP, AMP and a mixture thereof.

* * * * *

UNITED STATES PATENT AND TRADEMARK OFFICE
CERTIFICATE OF CORRECTION

PATENT NO. : 5,316,907
DATED : May 31, 1994
INVENTOR(S) : Lurie et al.

It is certified that error appears in the above-indentified patent and that said Letters Patent is hereby corrected as shown below:

Column 1, line 53, delete "(AND+)" and insert --(NAD$^+$)--

Column 5, lines 11-13, delete "Pyruvate Kinase" should be inserted to the right of the up arrow therefor.

Under Column 11, Line 3, please delete "mE" and insert --mM-- therefor.

Signed and Sealed this

Fourth Day of February, 1997

Attest:

BRUCE LEHMAN

*Attesting Officer*  *Commissioner of Patents and Trademarks*